United States Patent
Paust et al.

(10) Patent No.: US 6,740,774 B1
(45) Date of Patent: May 25, 2004

(54) PREPARATION OF N-ACYLAMINO ACID ESTERS AND N-ACYLAMINO ACETALS

(75) Inventors: Joachim Paust, Neuhofen (DE); Hansgeorg Ernst, Speyer (DE); Reinhard Kaczmarek, Hassloch (DE); Hagen Jaedicke, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 431 days.

(21) Appl. No.: 09/639,681

(22) Filed: Aug. 16, 2000

(30) Foreign Application Priority Data

Aug. 26, 1999 (DE) .......................... 199 40 641

(51) Int. Cl.$^7$ ............................................ C07C 229/00
(52) U.S. Cl. ..................................................... 560/170
(58) Field of Search ......................................... 560/170

(56) References Cited

FOREIGN PATENT DOCUMENTS

| DE | 11 17 134 | 11/1961 |
| DE | 31 45736 | 5/1983 |
| DE | 42 33 771 | 4/1994 |
| EP | 332 083 | 9/1989 |
| EP | 709 367 | 5/1996 |
| GB | 2 252 770 | 8/1992 |
| WO | WO 96/24074 | * 8/1996 |

OTHER PUBLICATIONS

Plaquevent et al, New J. Chem, 1991, vol. 15, pp. 579–585.*
Plaquevent et al., New J. Chem. vol. 15, 1991, pp. 579–585.*
Kleeman et al. "Ullmann's Encyclopedia of Industrial Chemistry" (1985) vol. A2, pp. 57–97.
Yoneda et al. "Autorecycling System for the Synthesis of α–Amin–acids by the Reductive Amination of α–Keto–acids catalysed by 1,5–Dihydro–5–deazaflavin" Journal of Chemical Communication (1982) pp. 927–929.
Konig et al. "Technisch bedeutsame Vitamin B$_6$–Synthesen" Chemiker Zeitung vol. 100 (1976) pp. 105–111.
Ugi et al. "Neuere Methoden der präparativen organischen Chemie IV" Angew. Chem. No. 77(1965) pp. 492–504.
Aizpurua et al. "Reagents and Synthetic Method 30. Practical and Improved Method for Formylating Amino Compounds By Means Of Formic Acid–Dimethylformamide System" Synthetic Compounds vol. 19 (1983) pp. 745–752.
Buck et al. Photochemistry of Acylazider. VIII Do Adylnitrenes React like 1,3–Dipoles? Journal für Praktische Chemi Chemiker–Zeitung vol. 336 (1994) pp. 678–685.
Shoji et al. "N–Fatty Acyl Compounds Inhibit Myristoyl Acylation of pp60 and Reduce Tumorigenicity of Rous Sarmoa Virus–Infected Cells" Biochemistry International vol. 23 (1991) pp. 15–23.
Plaquevent et al. "Creation Non–Classique e Liaison Peptidiques Par Isomerisation Oxaziridine–Amide: Études Modéles et Synthése Formelle De L'Aspartame" New J. Chem. vol. 15 (1991) pp. 579–585.
Michaelides et al. "Synthesis and Pharmacological Evaluation of 1–(aminoethyl)–3,4–dihydro–5–hydroxy–1 H–2–bonzopyrans as Dopamine D1 Selective Ligands" J. Med. Chem. vol. 34 (1991) pp. 2946–2953.

* cited by examiner

Primary Examiner—Paul Killos
Assistant Examiner—Hector M. Reyes
(74) Attorney, Agent, or Firm—Keil & Weinkauf

(57) ABSTRACT

A process for preparing N-acyl derivatives of the formula I,

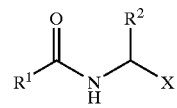

I in which the substituents independently of one another have the following meanings:

X is $CH(OR^3)_2$, $COOR^3$;
$R^1$ is hydrogen, $C_1$–$C_{12}$-alkyl, aryl, unsubstituted or substituted;
$R^2$ is hydrogen, $C_1$–$C_{12}$-alkyl, aryl, unsubstituted or substituted;
$R^3$ is $C_1$–$C_{12}$-alkyl,
which comprises reacting a carboxamide $R^1$—$CONH_2$ of the formula II with a glyoxal monoacetal derivative of the formula III,

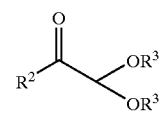

III in the presence of a carboxylic acid $R^4$—COOH of the formula IV where $R^4$=$C_1$–$C_{12}$-alkyl, where the substituents $R^1$ to $R^3$ are as defined above, is described.

13 Claims, No Drawings

PREPARATION OF N-ACYLAMINO ACID ESTERS AND N-ACYLAMINO ACETALS

The invention relates to a process for preparing N-acylamino acid esters and N-acylamino acetals.

A large number of different methods for synthesizing amino acids and their esters are known. A review is given, inter alia, in Ullmanns Encyclopedia of Industrial Chemistry, Vol. A2, 57–97, VCH Weinheim 1985.

Industrial syntheses of D,L-α-amino acids, for example the Strecker synthesis, use aldehydes as starting materials, which are reacted with $NH_3$ and HCN to give aminonitriles. The nitrile group can subsequently be reacted with alcohols or water to give the corresponding esters and amino acids, respectively.

DE-A-3145736 describes a process for preparing N-formyl-α-amino acid esters by reacting aminonitriles—for example from the Strecker synthesis—with an appropriate alcohol and formamide in the presence of hydrogen chloride.

Also known is the preparation of N-formyl-D,L-alanine from pyruvic acid by boiling with ammonium formate in formic acid [F. Yoneda and K. Kuroda, J. Chem. Soc. Chem. Commun., 1982, 927–929].

N-Formylalanine esters are used, inter alia, for preparing vitamin $B_6$ (Pyridoxine) [Review by König and Böll, Chem. Ztg. 100 (1976), 107/8] and isocyanic acid, for example according to Ugi, Angew. Chem. 77 (1965), 492.

The processes described have the disadvantage that the starting materials used are finished amino acids or precursors thereof—for example cyanohydrins or aminonitriles from the Strecker synthesis—which have to be prepared beforehand in a separate process.

It is an object of the present invention to provide a process for preparing N-acylamino acid esters and N-acylamino acetals which can easily be carried out on an industrial scale, using readily-obtainable starting materials.

We have found that this object is achieved by a process for preparing N-acyl derivatives of the formula I

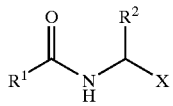

I in which the substituents independently of one another have the following meanings:

X is $CH(OR^3)_2$, $COOR^3$;

$R^1$ is hydrogen, $C_1-C_{12}$-alkyl, aryl, unsubstituted or substituted;

$R^2$ is hydrogen, $C_1-C_{12}$-alkyl, aryl, unsubstituted or substituted;

$R^3$ is $C_1-C_{12}$-alkyl, which comprises reacting a carboxamide $R^1$—$CONH_2$ of the formula II with a glyoxal monoacetal derivative of the formula III,

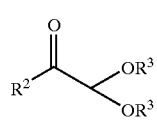

III in the presence of a carboxylic acid $R^4$—COOH of the formula IV where $R^4=C_1-C_{12}$-alkyl, where the substituents $R^1$ to $R^3$ are as defined above.

Alkyl radicals for $R^1$ to $R^4$ which may be mentioned are branched or straight-chain $C_1-C_{12}$-alkyl chains, for example methyl, ethyl, n-propyl, 1-methylethyl, n-butyl, 1-methylpropyl, 2 methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, 2-ethylhexyl, n-nonyl, n-decyl, n-undecyl and n-dodecyl.

The alkyl chains mentioned above can be unsubstituted, hydroxylated or substituted by mercapto groups. Preferred examples which may be mentioned are hydroxymethyl, hydroxyethyl, such as [$CH_3$—CH(OH)— or $CH_2$(OH)—$CH_2$] or mercaptomethyl radicals.

If the radical X in the formula I is $CH(OR^3)_2$, the substituents $R^3$ together with the oxygen atoms to which they are attached may also form a 5- or 6-membered ring. Starting materials used in this case are, for example, cyclic glyoxal monoacetals of the general formulae IIIa to IIIc.

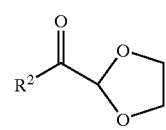

IIIa

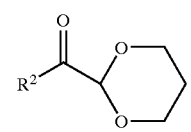

IIIb

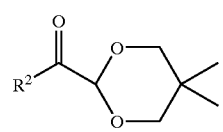

IIIc

Aryl for $R^1$ and $R^2$ is to be understood as an aromatic ring or ring system having 6 to 18 carbon atoms in the ring system, for example phenyl or naphthyl, which may be unsubstituted or substituted by one or more radicals, such as halogen, for example fluorine, chlorine or bromine, cyano, nitro, amino, $C_1-C_4$-alkylamino, $C_1-C_4$-dialkylamino, hydroxyl, $C_1-C_4$-alkyl, $C_1-C_4$-alkoxy or other radicals.

Preferred radicals for $R^1$ are hydrogen and the branched or straight-chain $C_1-C_8$-alkyl chains mentioned in the list above, particularly preferably $C_1-C_3$-alkyl chains. Very particularly preferred radicals for $R^1$ are hydrogen, methyl and ethyl.

Preferred radicals for $R^2$ are phenyl and the branched or straight-chain $C_1-C_8$-alkyl chains from the list mentioned above, particularly preferably $C_1-C_3$-alkyl chains. A very particularly preferred radical for $R^2$ is methyl.

Preferred alkyl radicals for $R^3$ are the branched or straight-chain $C_1-C_8$-alkyl chains from the list mentioned above, particularly preferably $C_3-C_8$-alkyl chains, such as, for example, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, n-heptyl, n-octyl or 2-ethylhexyl.

Preferred radicals for $R^4$ are the branched or straigh-chain $C_1-C_8$-alkyl chains from the list mentioned above, particularly preferably $C_1$–$C_3$-alkyl chains. Very particularly preferably radicals for $R^1$ are methyl, ethyl, n-propyl and isopropyl.

Depending on the amount of carboxamide $R^1$—$CONH_2$ and carboxylic acid $R^4$—COOH employed, the formation of the different N-acyl derivatives of the formula I can be controlled in a targeted manner.

Thus, contrary to expectation, it has been found that reaction of an amount of carboxamide $R^1$—$CONH_2$ and carboxylic acid $R^4$—COOH employed of in each case from 250 to 800 mol %, preferably from 400 to 600 mol %, based on the acetal of the formula II employed, gives N-acylamino acid esters of the formula I where X=$COOR^3$.

A particularly advantageous embodiment of the process was found to be the use of the carboxamide $R^1$—$CONH_2$ and the carboxylic acid $R^4$—COOH in identical molar proportions.

The process according to the invention is particularly suitable for preparing N-formyl-α-aminopropionic acid esters of the formula Ia Ia in which the substituent $R^3$ is $C_1$–$C_8$-alkyl, preferably $C_3$–$C_8$-alkyl.

Formation of the N-acylamino acetals of the formula I where X=CH($OR^3$)$_2$ is preferred when the amount of carboxamide $R^1$—$CONH_2$ and carboxylic acid $R^4$—COOH employed is in each case from 50 to 250 mol %, preferably from 100 to 200 mol %, based on the acetal of the formula II employed. In this case, too, it is particularly advantageous to employ carboxamide $R^1$—CONH2 and carboxylic acid $R^4$—COOH in the reaction in a molar ratio of 1:1.

In the case of the N-acylamino acetals of the formula I, the process according to the invention is advantageously suitable for preparing N-formyl-2-aminopropionaldehyde acetals of the formula Ib Ib in which the substituent $R^3$ is $C_1$–$C_8$-alkyl, preferably $C_3$–$C_8$-alkyl.

The conversion both into the N-acylamino acid esters and into the N-acylamino acetals is carried out at from 40 to 200° C., preferably from 60 to 150° C.

According to the invention, the reaction is carried out in a pressure range of from 200 to 1000 mbar, preferably between 500 and 1000 mbar, particularly preferably at atmospheric pressure.

The reaction can be carried out with or without additional solvent. The reaction is preferably carried out without adding a solvent.

Moreover, the process according to the invention can be carried out advantageously as a "one-pot process", giving both N-acylamino acid esters and the novel N-acylamino acetals in excellent yields.

The isolation of the desired end product is carried out in a manner known per se. In the case of liquid reaction products, the esters or acetals formed are usually purified by distillation.

The invention also provides N-acyl derivatives of the formula Ic,

Ic in which the substituents independently of one another have the following meanings:

$R^1$ is hydrogen, $C_1$–$C_{12}$-alkyl, aryl, unsubstituted or substituted;

$R^2$ is hydrogen, $C_1$–$C_{12}$-alkyl, aryl, unsubstituted or substituted;

$R^3$ is $C_1$–$C_{12}$-alkyl.

Preference is given to N-acyl derivatives of the formula Ic, in which the substituents independently of one another have the following meanings:

$R^1$ is hydrogen, $C_1$–$C_8$-alkyl;

$R^2$ and $R^3$ are $C_1$–$C_8$-alkyl.

With respect to the exact definition of the substituents $R^1$ to $R^3$, both in the general and the preferred embodiments, the definitions given at the outset for the compound I should be referred to.

The N-acylamino acetals of the formula Ic are suitable for use as intermediates for preparing oxazoles.

The following examples are used to illustrate the subject matter of the present invention in more detail.

EXAMPLE 1

Butyl N-formyl-D,L-alaninate from Methylglyoxal di-n-butyl Acetal.

100 g of methylglyoxal dibutyl acetal (purity 93.5%, prepared according to EP 036539) were mixed with 100 g of formamide and admixed with 100 g of formic acid over a period of 10 min. The temperature of the mixture increased to 40° C., and the mixture was then heated to reflux temperature within 20 min. After a reaction time of 2 hours, the reaction mixture, which had been cooled to room temperature, was washed with dilute sodium carbonate solution, and the desired product was distilled under reduced pressure at 2 mbar. This gave 74.5 g of pure butyl N-formyl-D,L-alaninate (93% of theory).

EXAMPLE 2

2-ethylhexyl N-formyl-D,L-alaninate from Methylglyoxal di-2-ethylhexyl Acetal 50 g of methylglyoxal di-2-ethylhexyl acetal (purity 92%) were boiled under reflux with 30 g of formamide and 30 g of formic acid for 2.5 hours. The mixture was washed with 200 ml of sodium carbonate solution and distilled. From the main fraction, 29.8 g of 2-ethylhexyl N-formyl-D,L-alaninate (89% of theory) were isolated.

EXAMPLE 3

N-formylaminopropionaldehyde di-n-butyl Acetal from Methylglyoxal di-n-butyl Acetal 100 g of methylglyoxal dibutyl acetal (purity 93.5%, prepared according to EP 036539) were mixed with 50 g of formamide and admixed with 50 g of formic acid over a period of 10 min. The temperature of the mixture increased to 40° C., and the mixture was then heated to reflux temperature within 20 min. After a reaction time of 2 hours, the reaction mixture, which had been cooled to room temperature, was washed with dilute sodium carbonate solution, and the desired product was distilled under reduced pressure at 2 mbar. This gave 39 g of N-formylaminopropionaldehyde di-n-butyl acetal.

We claim:

1. A process for preparing N-acyl derivatives of the formula I,

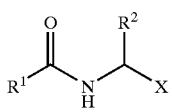

in which the substituents independently of one another have the following meanings:
X is $CH(OR^3)_2$, $COOR^3$;
$R^1$ is hydrogen, optionally substituted $C_1$–$C_{12}$-alkyl, optionally substituted aryl;
$R^2$ is hydrogen, optionally substituted $C_1$–$C_{12}$-alkyl, optionally substituted aryl;
$R^3$ is optionally substituted $C_1$–$C_{12}$-alkyl,
or, when X denotes $CH(OR^3)_2$, the substituents $R^3$ together with the oxygen atoms to which they are bonded and with the carbon atom to which the oxygen atoms are bonded form a 5- or 6-membered ring;
which comprises reacting a carboxamide $R^1$—$CONH_2$ of the formula II with a glyoxal monoacetal derivative of the formula III,

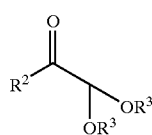

in the presence of a carboxylic acid $R^4$—COOH of the formula IV where $R^4$ is hydrogen or optionally substituted $C_1$–$C_{12}$-alkyl, where the substituents $R^1$ to $R^3$ are as defined above.

2. A process as claimed in claim 1, wherein the substituents have the following meanings:
$R^1$ is hydrogen, optionally substituted $C_1$–$C_8$-alkyl;
$R^2$ is optionally substituted $C_1$–$C_8$-alkyl, optionally substituted aryl;
$R^3$ and $R^4$ are optionally substituted $C_1$–$C_8$-alkyl.

3. A process as claimed in claim 2, wherein the substituents have the following meanings:
$R^1$ is hydrogen;
$R^2$ to $R^4$ are $C_1$–$C_8$-alkyl.

4. A process as claimed in claim 2 for preparing N-formyl-α-aminopropionic acid esters of formula Ia

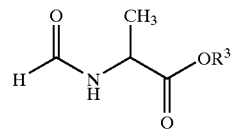

in which the substituent $R^3$ is $C_1$–$C_8$-alkyl.

5. A process as claimed in claim 1, wherein the substituents have the following meanings:
X is $CH(OR^3)_2$;
$R^1$ is hydrogen, optionally substituted $C_1$–$C_8$-alkyl;
$R^2$ is optionally substituted $C_1$–$C_8$-alkyl, optionally substituted aryl;
$R^3$ and $R^4$ are optionally substituted $C_1$–$C_8$-alkyl.

6. A process as claimed in claim 5, wherein the substituents have the following meanings:
$R^1$ is hydrogen;
$R^2$ to $R^4$ are $C_1$–$C_8$-alkyl.

7. A process as claimed in claim 5 for preparing N-formyl-2-aminopropionaldehyde derivatives of the formula Ib

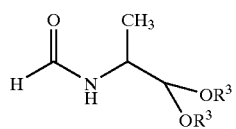

in which the substituent $R^3$ is $C_1$–$C_8$-alkyl.

8. A process as claimed in claim 2, wherein the amount of the respective carboxamide $R^1$—$CONH_2$ and carboxylic acid $R^4$—COOH employed is from 250 to 800 mol %, based on the acetal of the formula II employed.

9. A process as claimed in claim 8, wherein the amount of the respective carboxamide $R^1$—$CONH_2$ and carboxylic acid $R^4$—COOH employed is from 400 to 600 mol %, based on the acetal of the formula II employed.

10. A process as claimed in claim 8, wherein the carboxamide $R^1$—$CONH_2$ and the carboxylic acid $R^4$—COOH are employed in the reaction in a molar ratio of 1:1.

11. A process as claimed in claim 5, wherein the amount of the respective carboxamide $R^1$—$CONH_2$ and carboxylic acid $R^4$—COOH employed is from 50 to 250 mol %, based on the acetal of the formula II employed.

12. A process as claimed in claim 11, wherein the amount of the respective carboxamide $R^1$—$CONH_2$ and carboxylic acid $R^4$—COOH employed is from 100 to 200 mol %, based on the acetal of the formula II employed.

13. A process as claimed in claim 11, wherein the carboxamide $R^1$—$CONH_2$ and the carboxylic acid $R^4$—COOH are employed in the reaction in a molar ratio of 1:1.

* * * * *